United States Patent [19]

Gabele et al.

[11] Patent Number: 4,948,566
[45] Date of Patent: Aug. 14, 1990

[54] STERILIZING SYSTEM FOR STERILIZING CONTAINERS

[75] Inventors: Lorenz Gabele, Sauldorf; Häusler; Walter Lohrer, both of Tuttlingen; Johannes Seibert, Wurmlingen; Harald Stallforth, Tuttlingen; Wolfgang Taschner, Tuttlingen; Otmar Wawrik, Hanau; Wilfried Wöfle, Bad Dürrheim, all of Fed. Rep. of Germany

[73] Assignee: Aesculap-Werke AG, Tuttlingen, Fed. Rep. of Germany

[21] Appl. No.: 100,490

[22] Filed: Sep. 24, 1987

[30] Foreign Application Priority Data

Sep. 26, 1986 [DE] Fed. Rep. of Germany ....... 3632675

[51] Int. Cl.⁵ .......................... B65D 51/16; A61L 2/06
[52] U.S. Cl. ..................................... 422/107; 422/295; 422/298; 422/299; 422/310; 220/366; 220/DIG. 27; 220/202
[58] Field of Search ............... 422/107, 295, 298, 299, 422/310; 220/366, DIG. 27, 202

[56] References Cited

U.S. PATENT DOCUMENTS 4,251,482 2/1981 Sanderson et al. .
4,349,118 9/1982 Sanderson et al. .
4,512,498 4/1985 Leibirger ..................... 422/300 X
4,551,311 11/1985 Lorenz ............................. 422/300

FOREIGN PATENT DOCUMENTS 1217551 4/1965 Fed. Rep. of Germany .
1642161 3/1967 Fed. Rep. of Germany .
3202430 1/1982 Fed. Rep. of Germany .

Primary Examiner—Robert J. Warden
Assistant Examiner—Lynn M. Kummert
Attorney, Agent, or Firm—Wolf, Greenfield & Sacks

[57] ABSTRACT

The invention relates to a sterilizing system for sterilizing containers. In accordance with the invention, an external actuating element is provided in an autoclave chamber structure to hold special closure elements and/or the container lid in an open position and to bring them into a closed position before the autoclave is opened.

8 Claims, 3 Drawing Sheets

STERILIZING SYSTEM FOR STERILIZING CONTAINERS

BACKGROUND OF THE INVENTION:

The invention relates to a device for sterilizing the interior and the contents of sterilizing containers for medical purposes in an autoclave chamber structure by means of a vaporous or gaseous sterilizing medium which enters the interior of the sterilizing container during sterilization through at least one opening which is sealingly closable by means of a closure element constituting part of the sterilizing container in order to maintain the sterile condition after completion of a sterilizing procedure.

Sterilizing containers which generally have clamping devices as closure devices are known. The clamping devices are arranged on the bottom section of the container and engage by means of a hook-shaped clamping element recesses in the container lid, thereby sealingly fixing the latter on the bottom section when the closure devices are in the closed position. It is further known to provide detent elements, on the one hand, on the lid of a sterilizing container and, on the other hand, on the bottom section of the latter so as to establish a detent connection. The detent elements sealingly fix the lid in the detained state on the bottom section.

It is also known (German Offenlegungsschrift (unexamined Patent Application) 3,202,430) to provide sterilizing containers with additional closure devices which serve to automatically open and close, in dependence upon the temperature, an opening in the container, for example, by means of a bimetal element or the like, to, for example, allow condensate to drip off through an outlet opening at the bottom of the container. When the sterilizing container is located inside an autoclave structure, these automatic closure devices serve to open an opening during a certain phase of a sterilizing cycle and to later automatically close this opening again before the autoclave is opened so as to prevent new germs from entering the interior of the sterilizing container after the autoclave has been opened.

The hitherto known, automatically operating closure devices have not proven fully satisfactory in all cases. Firstly, the openings which are to be opened and closed by such closure devices can only be relatively small. Therefore, in some cases there is no guarantee that the objects to be sterilized, in particular, the medical instruments, are fully rinsed by the sterilizing medium circulating in the autoclave and that the germs adhering to them are reliably killed. Secondly, the bimetals used behave with considerable delay. Hence, in the case of hot sterilization, an extended cooling-off phase is required, to start with, and, even then, there is still no guarantee that the openings are actually completely closed when the sterilizing container is removed from the autoclave.

SUMMARY OF THE INVENTION:

Taking the prior art and the problems set forth hereinabove as a starting point, the object underlying the invention is to provide an improved device for sterilization of sterilizing containers for medical purposes which, on the one hand, guarantees that the container interior is fully accessible to the sterilizing atmosphere in an autoclave during the sterilizing procedure and which, on the other hand, ensures reliable closure of the container before the autoclave is opened.

This object is attained in the device referred to at the beginning, in accordance with the invention, by provision of an external actuating element constituting part of the autoclave chamber structure, which actuating element can be brought into a first position relative to the sterilizing container, in which first position the closure element can be fixed in the open state for the duration of the sterilizing procedure, and which actuating element can be brought after completion of the sterilizing procedure, with the autoclave chamber structure in the sealingly closed state, into a second position, this being controlled by at least one operating parameter of the autoclave chamber structure which is ascertained by an associated sensor constituting part of the autoclave chamber structure, in which second position the closure element is actuatable to sealingly close the opening.

A special advantage of the inventive device is that no special limitations need to be taken into consideration with respect to the dimensions of the closure element and hence with respect to the dimensions of the opening for the sterilizing medium since the external actuating element and the associated actuating devices can be of sufficiently strong construction to hold the closure element, possibly against a spring bias, in an open position or to bring the closure element into a closed position, and in particular, the entire lid of the sterilizing container may serve as closure element. A further advantage of the inventive device is that the actuating element and the associated devices can, as elements of the autoclave chamber structure, be of more robust, more precise and possibly also more expensive design than the hitherto used automatic closing devices on the containers themselves, without any increase in the total cost of the sterilization.

In a preferred embodiment of an inventive device serving specially for sterilization of sterilizing containers with a closure element which is spring biased in the direction of closure, an elongate member is provided as actuating element. During the sterilizing procedure, the elongate member rests against the closure element—thereby holding the latter in its open position—and after completion of the sterilizing procedure is retractable into a neutral position.

Another advantageous device according to the invention for sterilization of a sterilizing container with a lid acting as closure element for an opening in the bottom section of the container and having at least one opening at the side for cooperation with a closure element provided on the bottom section of the container is characterized by provision of an elongate member as actuating element, with the elongate member being in engagement with the opening in the lid during the sterilizing procedure to hold the lid in a raised position and with the elongate member being retractable into a neutral position to close the lid after completion of the sterilizing procedure.

In a further advantageous embodiment of a device according to the invention for sterilization of a sterilizing container with a lid acting as closure element for an opening in the bottom section of the container and having at least one detent element for detent engagement with a counter-element provided on the bottom section of the container, the actuating element is in the form of an elongate member by means of which a force can be applied to the lid after completion of a sterilizing procedure to effect detent engagement of the lid with the bottom section of the container.

The actuating elements of the various inventive devices adapted to the respective type of container to be sterilized are preferably provided at the corresponding points on a rack located in the autoclave chamber of the autoclave chamber structure. In an advantageous development of the invention, the rack is equipped with corresponding positioning devices for the individual containers. Hence short displacement of the actuating elements in comparison with the container dimensions is adequate to open and close the closure elements.

In the various advantageous embodiments of devices according to the invention, there is the possibility, depending on the given factors, of ascertaining by means of the sensor, in particular, one of the following operating parameters: the temperature, the pressure, the moisture, the state of a closure element serving to sealingly close the autoclave chamber or the state of a closure device for the closure element. In particular, it is also possible to evaluate several operating parameters simultaneously or in time succession and to control the actuating elements in dependence upon the combined monitoring and checking results.

In all of the inventive embodiments referred to hereinabove, there is the advantageous possibility of using electric transducers as sensors to convert the temperature values, the pressure values and the like into corresponding electric signals which, in a control system which, in this case, is to be provided in accordance with the invention, are evaluated, amplified and delivered to actuating devices for the actuating element. The control system can combine the output signals of several sensors in a specified manner so that an activating signal for the actuating devices is only delivered in the presence of a certain combination of operating parameters. It is also possible to evaluate individual parameters as a function of time and to generate an activating signal, for example, only if a specified minimum temperature has been reached at least twice in the course of a sterilizing procedure.

In an advantageous development of the inventive concept, the at least one sensor of an inventive device may be a simple door contact by means of which a circuit of a control system for the actuating element is opened or closed. In this case, the configuration of such a door contact is such that it responds before the ambient air can actually flow freely into the autoclave chamber, which is readily possible if, for example, a door of the autoclave chamber is provided with a seal which, during closure, is compressed to a certain extent and, during opening, first elastically regains its original shape before opening of the door to allow inflow of ambient air is actually effected. A corresponding contact may also be actuated by the locking devices of an autoclave door, in which case, there is likewise a certain time delay between the unlocking and the actual opening, which is sufficient for actuation of the actuating element.

In a corresponding manner, it also possible to provide an actuating device which operates purely mechanically and which automatically acts upon the actuating element when the autoclave door is opened and closed or locked and unlocked, thereby to effect sealed closure of the sterilizing container after completion of a sterilizing procedure before it is possible for non-sterilized ambient air to enter the container. The necessary displacement for the actuating element may also be achieved by suitable mechanical transmissions such as, for example, tilting levers and the like.

In particular, in an advantageous development of the invention using a purely mechanical sensor, it is possible, during closure of the autoclave, to tension a spring which during opening acts as an energy storing device to rapidly actuate the actuating element. If such a force or energy storing device is used, it then only remains necessary, on opening the autoclave door, to displace a locking element to an extremely short extent, to allow the full force of the energy storing device to act upon the actuating element. If, in a corresponding manner, electric sensors are used in combination with an electric control system, it is also possible to use electrical energy storing devices such as inductors or capacitors to make high energy available for a short time on closing the container.

Finally, in all of the embodiments of inventive sterilizing devices referred to hereinabove, there is the possibility of providing instead of one single external actuating element, several such actuating elements in order to act at several points on larger closure elements, for example, on opposite sides of a container lid to fix the latter on the bottom section of the container by means of detent devices provided on opposite sides of the container. The various actuating elements can be actuatable independently of one another or in time succession in order to lower the peak value of the energy requirement. In other cases it may be advantageous to design several actuating elements as parts of a single, for example, fork-shaped actuating member.

BRIEF DESCRIPTION OF THE DRAWINGS:

Further advantages and details of the invention are explained at greater length with reference to drawings, in which.

Figure 1:
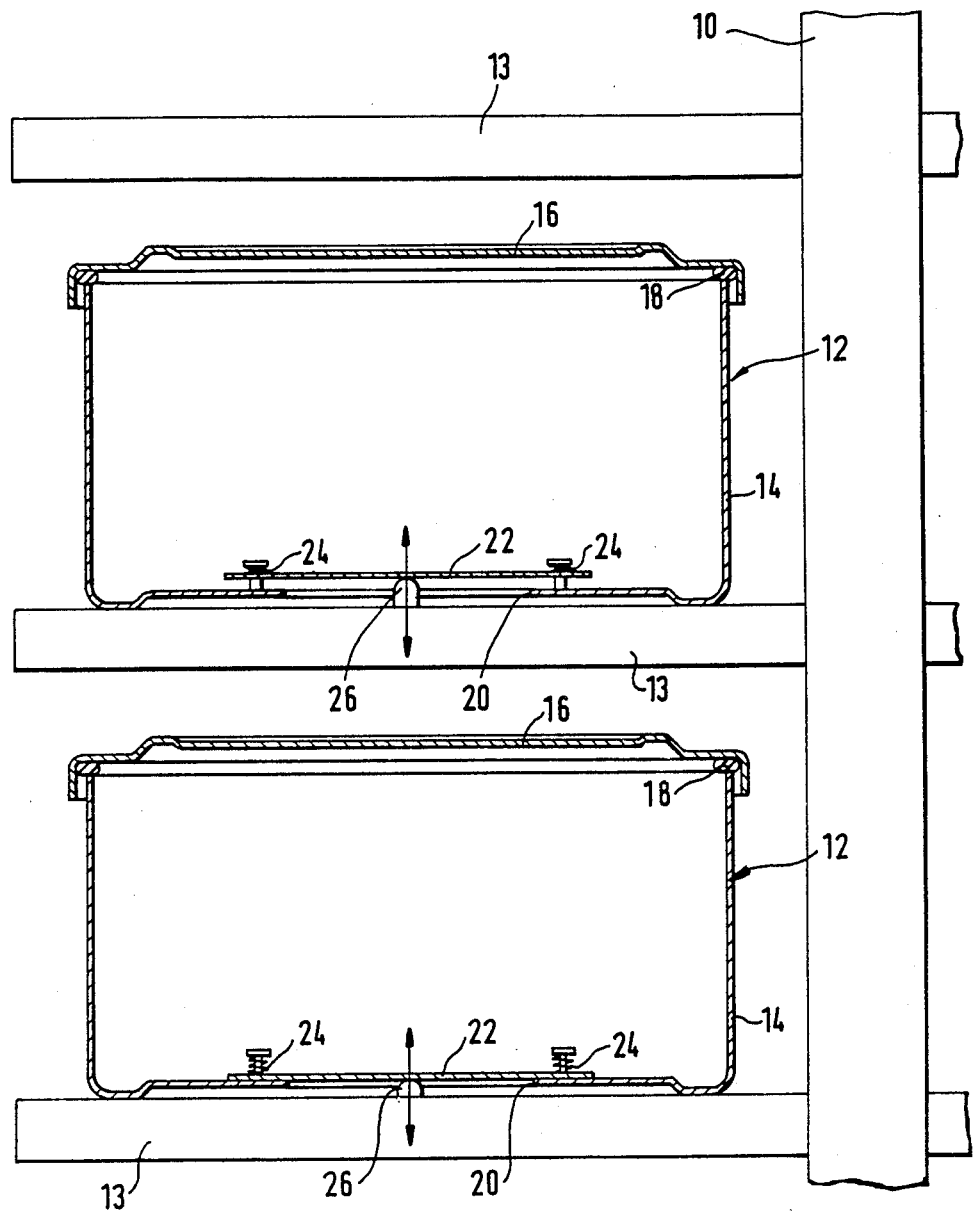
FIG. 1 is a schematic cross-sectional illustration of a sterilizing container with an associated inventive actuating device, in the open and closed states, respectively, on a rack of an autoclave chamber structure.

DESCRIPTION OF THE PREFERRED EMBODIMENTS:

FIG. 1 shows a section of a rack 10 as typically placed in the autoclave chamber of an autoclave, for accommodating in several tiers and typically in two rows beside each other, sterilizing containers 12 which are then jointly sterilized in the course of one sterilizing cycle. The sterilizing containers 12 stand on tiered shelves 13 (see FIG. 4).

Each sterilizing container comprises a bottom section 14 and a lid 16. Lid 16 is sealingly positioned on bottom section 14 by means of a seal 18. An opening 20 which is sealingly closable by a plate-shaped closure element or a closure plate 22 is provided in the bottom section 14 of container 12. The closure plate is biased in the direction of closure against the edge of opening 20 by means of helical springs 24 which act on its rear side or inner side. Hence the closure plate is normally closed, as illustrated in the lower one of the two containers 12 shown in FIG. 1.

In accordance with the invention, an actuating element in the form of an elongate member 26 is provided. The elongate member is movable by associated actuating devices, as indicated by a double arrow, between a neutral position shown in the lower part of FIG. 1, and a work position shown in the upper part of FIG. 1. In its work position, the elongate member 26 holds the closure plate 22 in an upper position against the force of springs 24, thereby enabling a sterilizing medium to flow through the thus provided gap between the edge of the opening 20 and the outer edge of the closure plate 22. When the elongate member 26 is moved out of its work position into its neutral position, springs 24 then press closure plate 22 into its closed position shown in the lower part of FIG. 1, whereby the container 12 is sealingly closed.

Figure 2:
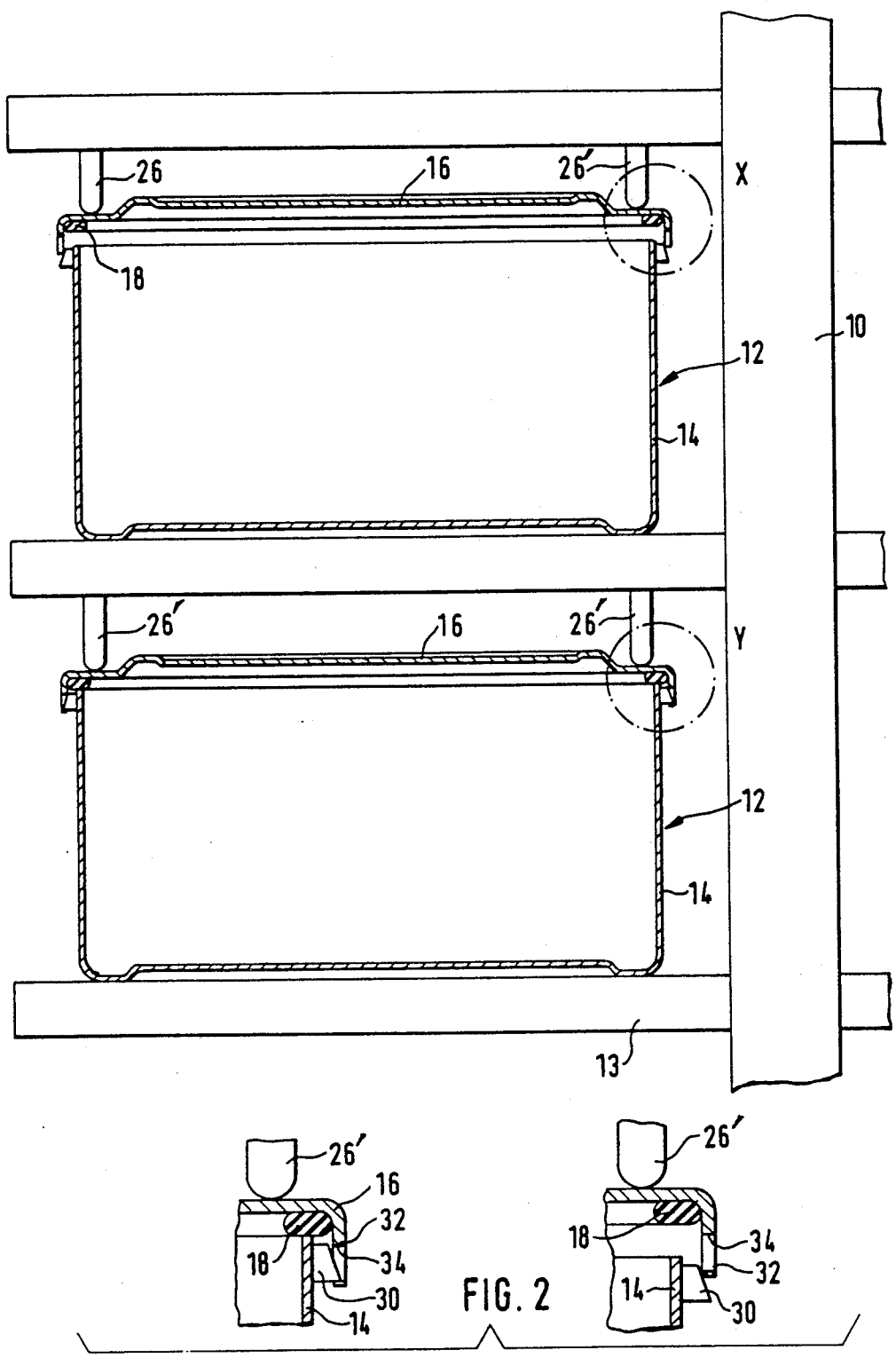
FIGS. 2 and 3 are illustrations similar to FIG. 1 of modified embodiments of sterilizing containers and actuating devices, with two important details shown on an enlarged scale in each of the Figures.

In the embodiment shown in FIG. 2, detent projections 30 are provided on the bottom section 14 of container 12. When the container is open (upper part of FIG. 2) the container lid 16 rests loosely with tongue-shaped, elastically deformable counter-elements 32 on the detent projections 30. Two actuating elements in the form of elongate members 26' are then in their neutral position. If the container is to be closed, the elongate members 26' are lowered in the downward direction—see FIG. 2—and the counter-elements 32 slide downwardly over inclined surfaces of detent projections 30 until detent projections 30 drop into an opening 34 provided for this purpose in the counter-elements. In this way, the lid 16 is sealed to the bottom section 14 of container 12 by a detent connection. The details of elements 30, 32 of the detent connection are illustrated as detail X for the open state of container 12 and as detail Y for the closed state of the container.

Figure 3:
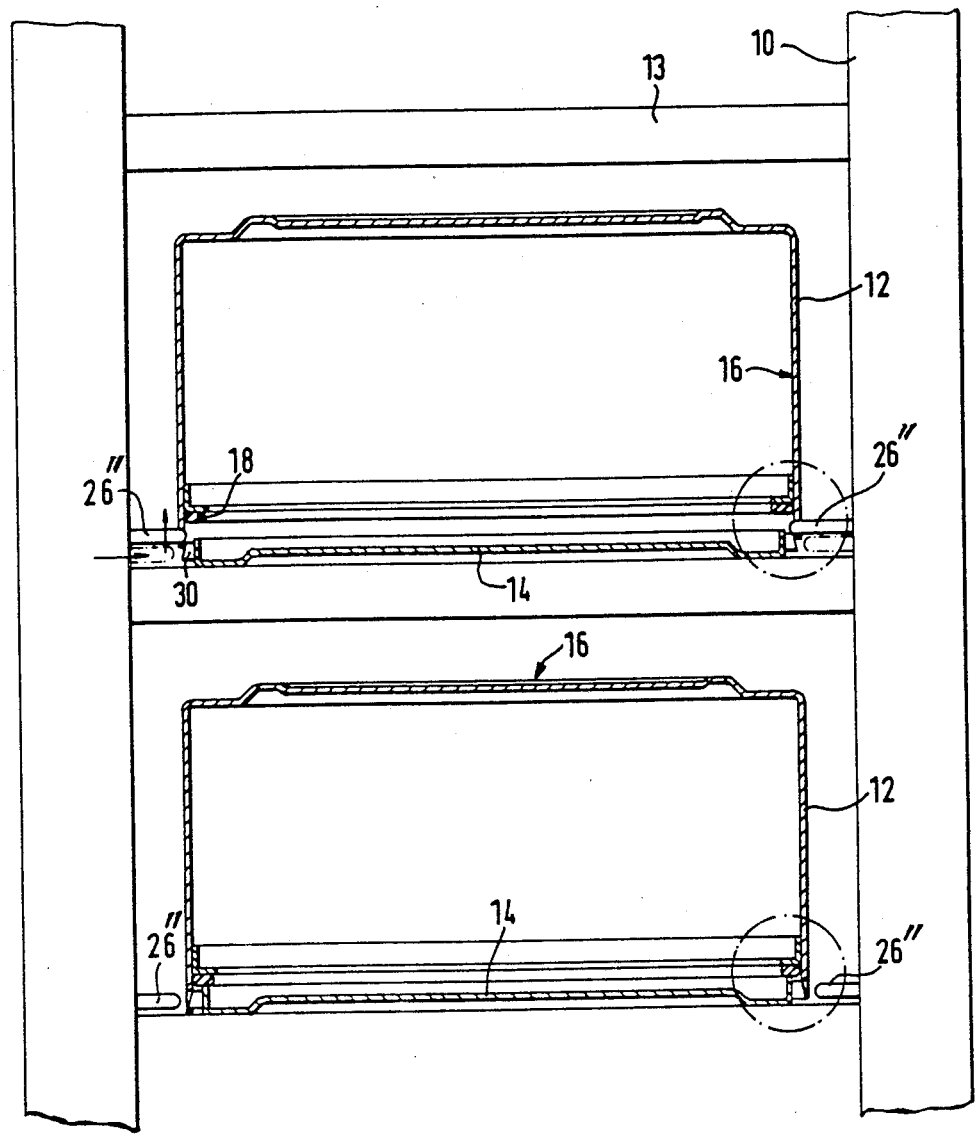
Figure 3:
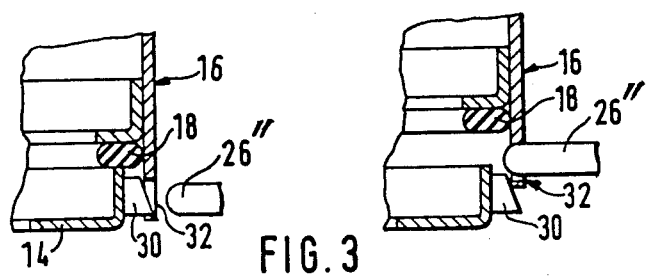

In the embodiment shown in FIG. 3, container 12 has a very flat bottom section 14 which is similarly provided with detent projections 30. In a corresponding manner, associated counter-elements 32 are also provided on the tub-shaped lid 16 to establish a sealing detent connection with the bottom section 14.

Differing from the embodiment shown in FIG. 2, the lid 16 in FIG. 3 is first held by means of the elongate actuating elements 26" in an upper position in which the container 12 is open—upper illustration in FIG. 3. If the container 12 is to be closed, the elongate members 26" are first moved downwarldy to pull the counter-elements 32 over the detent projections 30 and are then retracted outwardly after the detent connection has been established. When a closed container 12 is inserted into rack 10, elongate member 26" first moves inwardly and then upwardly. During the first step, the detent connection is released by elastic deformation of detent projections 30 and bottom section 14, respectively, whereupon the lid 13 is then raised. In FIG. 3, the details of the detent connection for the open and closed states of container 12 are likewise illustrated on an enlarged scale as details X and Y, respectively.

Figure 4:
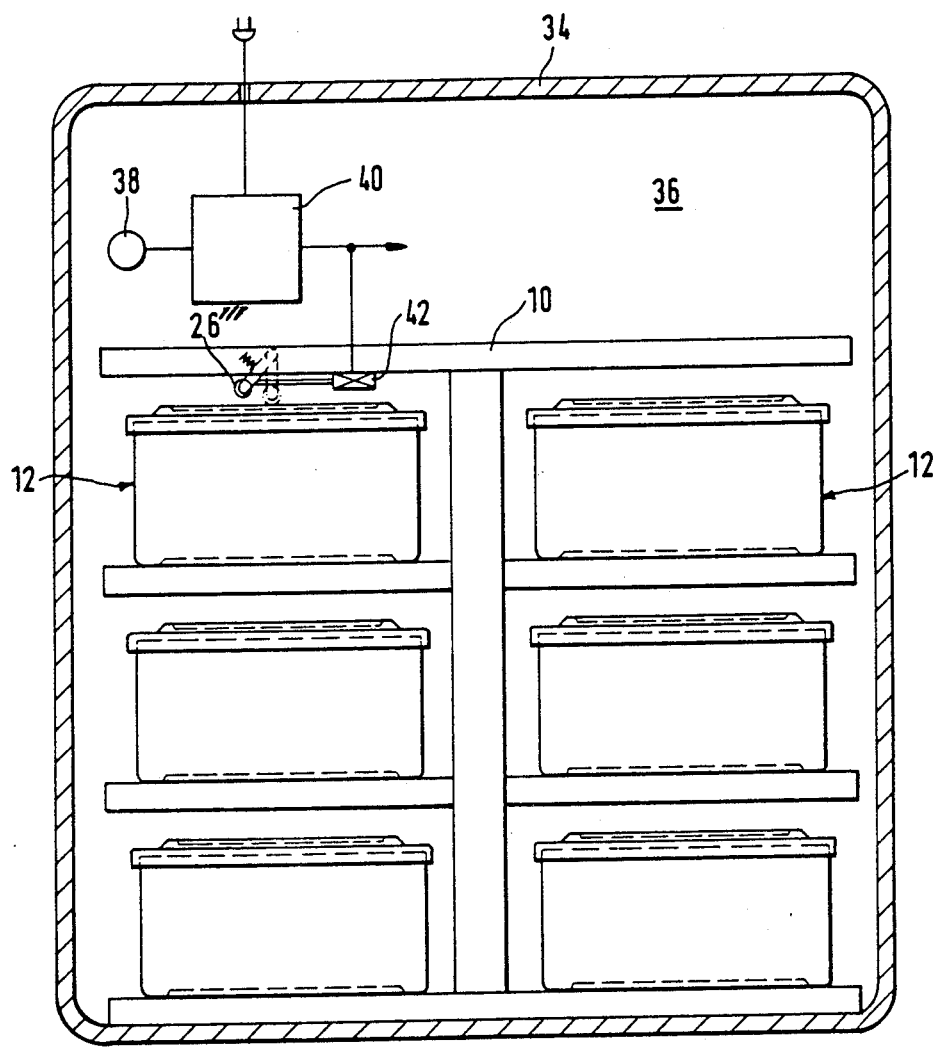
FIG. 4 is a highly schematic illustration of an autoclave chamber structure with a preferred embodiment of a device according to the invention.

FIG. 4 of the drawings shows in a highly schematic illustration an autoclave 34 defining an autoclave chamber 36 in which the rack 10 is located. In accordance with the invention, a sensor 38 is provided, for example, a temperature sensor which is connected to a control system 40 with a schematically indicated external voltage supply. The control system supplies output signals to an electromagnet 42 whose armature serves to pivot an actuating element 26''' from a neutral position indicated in unbroken lines into a work position indicated by dashed lines. The shown construction may be used, for example, in a container 12 such as that shown in FIG. 2 where the lid 16 first rests loosely on the detent projections 30 and can then be sealingly detained on the bottom section 14 by actuating element 26''' being pivoted into its work position. In the case of the device shown in FIG. 4, an associated actuating element with an electromagnet 42 activatable by control system 40 is, of course, provided for each of the containers 12. As explained at the beginning, all of the containers 12 are simultaneously closed when control system 40 on receiving a corresponding output signal from sensor 38 delivers an activating signal for the magnets 42.

If the energy available at the output of the control system is not or not readily sufficient to actuate all of the actuating devices simultaneously, there is also the possibility of activating the actuating devices sequentially by means of, for example, a multiplexer connected upstream thereof. In this case, early generation of the activating signal prior to the opening of the autoclave chamber is essential. For details of the configuration of the sensors and the associated control system and of the design of the energy storing devices, reference is made to the simultaneously filed application U.S.S.N. 097,635 filed Sept. 16, 1987 of the applicant company entitled "Sterilizing Container for Medical Purposes" where particulars are given at length in a somewhat different context.

What is claimed is:

1. A system for sterilizing the interior and the contents of sterilizing containers for medical purposes in an autoclave chamber structure by means of a vaporous or gaseous sterilizing medium which enters the interior of the sterilizing container during sterilization through at least one opening which is sealingly closable by means of a closure element constituting part of the sterilizing container in order to maintain the sterile condition after completion of a sterilizing procedure, wherein:

an external actuating element constituting part of said autoclave chamber structure is provided, said actuating element being movable along a first direction into a first position relative to said sterilizing container in which said closure element is fixable in the open state for the duration of the sterilizing procedure, and said actuating element being movable after completion of the sterilizing procedure, with the autoclave chamber structure in the sealingly closed state, into a second position, this being controlled by at least one operating parameter of said autoclave chamber structure which is ascertained by an associated sensor constituting part of said autoclave chamber structure, said closure element being actuatable in said second position to sealingly close said opening.

2. A system as defined in claim 1 for sterilization of sterilizing containers comprising a closure element which is spring biased along said first direction, wherein:

an elongate member is provided as an actuating element, said elongate member being positioned during the sterilizing procedure against said closure element, thereby holding said closure element in open position, and said elongate member being retractable into a neutral position after completion of the sterilizing procedure.

3. A system as defined in claim 1 for sterilization of a sterilizing container wherein said container has a lid with a side and a bottom section on which said lid seats when in a closed position, said lid acting as a closure element for means defining an opening in the bottom section of said container and having means defining at least one opening at said side for cooperation with a closure element provided on the bottom section of said container, and wherein:

an elongate member is provided as an actuating element, said elongate member being in engagement during a sterilizing procedure with said means defining at least one opening of said lid to hold said lid in a raised position, and said elongate member being retractable into a neutral position after completion of the sterilizing procedure in order to close said lid.

4. A system as defined in claim 1 for sterilization of a sterilizing container having a lid and a bottom section on which the lid seats comprising a lid acting as a closure element for means defining an opening in the bottom section of said container and having at least one detent element for detent engagement with a counterelement provided on the bottom section of said container, wherein:

said actuating element is in the form of an elongate member by means of which a force is applied to said lid after completion of a sterilizing procedure, to effect detent engagement of said lid with said bottom section of said container.

5. A system as defined in claim 1, wherein several sensors are provided, said sensors being connected to a control system by means of which an actuating device for said actuating element is actuatable.

6. A system as defined in claim 1, wherein:

said actuating element is provided on a rack located in the autoclave chamber of said autoclave chamber structure.

7. A system as defined in claim 6, wherein:

an associated actuating element is provided for each of said containers.

8. A system as defined in claim 1, wherein:

said sensor is in the form of a mechanical feeler element by means of which actuation of closure devices of said autoclave chamber structures is detected and converted into motion of said actuating element.

* * * * *